United States Patent [19]
Mares et al.

[11] Patent Number: 5,061,281
[45] Date of Patent: Oct. 29, 1991

[54] BIORESORBABLE POLYMERS AND IMPLANTATION DEVICES THEREOF

[75] Inventors: Frank Mares, Whippany; Reginald T. Tang, Warren, both of N.J.; Tin-Ho Chiu, Reading, Mass.; Theodore Largman, Morristown; Emery Nyilas, deceased, late of Austin, Tex., by Ilona Nyilas, executor

[73] Assignee: Allied-Signal Inc., Morris Township, Morris County, N.J.

[21] Appl. No.: 942,907

[22] Filed: Dec. 17, 1986

Related U.S. Application Data

[63] Continuation-in-part of Ser. No. 809,978, Dec. 17, 1985.

[51] Int. Cl.⁵ .......................... A61F 2/02; A61F 2/04
[52] U.S. Cl. ........................................ 623/11; 623/12; 523/113; 523/114; 606/152
[58] Field of Search ............... 623/11, 66, 16, 12; 528/354, 272, 302, 303; 523/113, 114, 115; 128/334 R, 334 C, 335.5, DIG. 8

[56] References Cited

U.S. PATENT DOCUMENTS

| | | |
|---|---|---|
| 2,668,162 | 2/1954 | Lowe . |
| 2,703,316 | 3/1955 | Schneider . |
| 3,463,158 | 8/1969 | Schmitt et al. ............... 623/66 X |
| 3,531,561 | 9/1970 | Trehu . |
| 3,636,956 | 1/1972 | Schneider . |
| 3,792,010 | 2/1974 | Wasserman et al. . |
| 3,797,499 | 3/1974 | Schneider . |
| 3,867,190 | 2/1975 | Schmitt et al. . |
| 3,883,901 | 5/1975 | Coquard et al. . |
| 4,032,993 | 7/1977 | Coquard et al. . |
| 4,137,921 | 2/1979 | Okuzumi et al. . |
| 4,157,437 | 6/1979 | Okuzumi et al. . |
| 4,243,775 | 1/1981 | Rosensaft et al. . |
| 4,273,920 | 6/1981 | Nevin . |
| 4,279,249 | 7/1981 | Vert et al. . |
| 4,331,652 | 5/1982 | Ludwig et al. . |
| 4,534,349 | 8/1985 | Barrows ..................... 128/334 C X |
| 4,643,734 | 2/1987 | Lin ..................................... 623/16 |

OTHER PUBLICATIONS

Nyilas et al., "Peripheral Nerve Repair with Bioresorbable Prosthesis", *Trans. Am. Soc. Artif. Intern. Organs*, vol. XXIX, Apr. 1983.

*Primary Examiner*—Alan W. Cannon
*Attorney, Agent, or Firm*—Richard C. Stewart; Gerhard H. Fuchs

[57] ABSTRACT

This invention relates to an implantable medical device capable of encouraging cellular growth and regeneration of function fabricated totally or in part from one or more bioresorbable polymers, as for example bioresorbable homopolymers derived from the polymerization of alpha-hydroxy carboxylic acids, where at least one of the polymers has an average molecular weight of from about 234,000 to about 320,000 as measured by gel permeation chromatography.

6 Claims, 1 Drawing Sheet

BIORESORBABLE POLYMERS AND IMPLANTATION DEVICES THEREOF

This is a continuation-in-part of Ser. No. 809,978, filed Dec. 17, 1985.

FIELD OF THE INVENTION

This invention relates to an improvement in the use of bioresorbable polymers for implantation into living tissue characterized in that a particular mixture of two or more polymers molecular is selected that demonstrates an unexpectedly beneficial effect on cell growth and therefore regeneration of function.

BACKGROUND OF THE INVENTION

The use of bioresorbable polymers for implantation in living tissue has steadily increased over the last few decades. Medical applications of such polymers include absorbable sutures, intraosseous implants and slow-release drug delivery systems.

More recently, their use has been extended to microtubular tissue regeneration guidance channels. For example, bioresorbable materials have been used in the repair of injured nerves. Nerves with severed axons, but intact somas, may retain the capability of regrowing from the proximal stump to reconnect distally. Structures have been fabricated that serve as conduits for the regrowth and reconnection of severed nerves. After accomplishing their function, these guides gradually disappear from the host.

To be effective, these devices, commonly known as nerve channels, nerve guidance channels, nerve guidance tubes, nerve guides, or nerve tubes, must be made from materials that meet a wide range of biological and physicochemical prerequisites. The material must be bioresorbable, nontoxic, noncarcinogenic, nonantigenic, and must demonstrate favorable mechanical properties such as flexibility, suturability, and amenability to custom fabrication.

Further, it has been recently appreciated that these materials also must be capable of supporting cellular growth, to the extent that they actually exert a "neurotropic" effect. After exerting such an effect, they must also retain structural integrity to the extent necessary to maximize the number of axons reaching the distal stump to restore nerve function. This requires guidance channel biodegradation/resorption rates compatible with axon growth rates.

Examples of absorbable materials used in nerve repair include collagen as disclosed by D. G. Kline and G. J. Hayes, "The Use of a Resorbable Wrapper for Peripheral Nerve Repair, Experimental Studies in Chimpanzees", *J. Neurosurgery* 21, 737 (1964). However, one of the major disadvantages inherent with collagenous materials is their potential antigenicity.

Two related patents, U.S. Pat. Nos. 4,033,938 and 3,960,152, disclose bioabsorbable polymers of unsymmetrically substituted 1,4-dioxane-2,5-diones which are broadly stated to be useful as tubes or sheets for surgical repair such as nerve and tendon splicing. A similar disclosure in U.S. Pat. No. 4,074,366 relates to poly(N-acetyl-D-glucosamine), i.e. chitin.

Other biodegradable polymers of particular interest for medical implantation purposes are homopolymers and copolymers of the alpha-hydroxy carboxylic acids, glycolic acid and lactic acid. These materials undergo hydrolytic scission to form metabolites normal to the body, which are therefore amenable to resorption.

A biodegradable polyglactin suture mesh shaped as a tube around a nerve defect to serve as a framework for proliferating cells has been reported in *Muscle and Nerve* 5, 54–57 (1982). However, less than satisfactory results were achieved in that some of the regenerating axons gained access to the meshes of the polyglactin tube causing the formation of minifascicles. A nerve cuff in the form of a smooth, rigid tube has also been fabricated from a copolymer of lactic and glycolic acids [*The Hand* 10, (3) 259 (1978)].

U.S. Pat. No. 4,481,353 discloses a bioresorbable polyester terpolymer that also includes an alpha-hydroxy carboxylic acid in conjunction with Krebs cycle dicarboxylic acids and aliphatic diols. These polyesters are useful in fabricating nerve guidance channels as well as other surgical articles such as sutures and ligatures.

Regenerated nerves have also been successfully obtained with nerve guides prepared from the homopolymer poly(DL-lactic acid), as measured by myelinated axon counts. The polymers used were obtained commercially, and had a weight average molecular weight of approximately 68,000, which was fractionated to a maximum weight average molecular weight of 113,000. In some cases, a bioresorbable plasticizer was added to impart flexibility and suturability. Studies conducted with a transected rat optic nerve using the nerve guide have shown that the formation of a cable is induced. The cable is composed of fibroblasts, macrophages, astrocytes, oligodendrocytes, collagen, Schwann cells, a connective tissue sheath and numerous blood vessels and myelinated and unmyelinated axons. *Transactions of the American Society of Artificial Internal Organs*, Vol. 29 (1983) pp. 307–313. Results with similar nerve guides, reported to have an weight average molecular weight of 100,000, are disclosed in *Plastic Reconstructive Surgery* 62, 173 (1984).

SUMMARY OF THE INVENTION

Apart from merely maintaining the mechanical integrity of the device itself, the present inventors have discovered that particular mixtures of two or more polymers, as well as the molecular weight of the polymers, used whether as a mixture or alone, has a marked physiological influence on the growth rate of living tissue, particularly nerve growth. The ability of the tissue to regenerate and even to regain function has been vastly encouraged through the use of a mixture of two or more polymers or of a single polymer or mixture of polymers within a specific molecular weight range.

This unexpectedly beneficial biological effect is attributed to a critical molecular weight range of the polymer, or to specific mixtures of polymers. Hence, the spectrum of applicability of such bioresorbable polymers involves implants to aid the regeneration of devitalized organs.

DETAILED DESCRIPTION OF THE PREFERRED EMBODIMENTS

Figure 1:
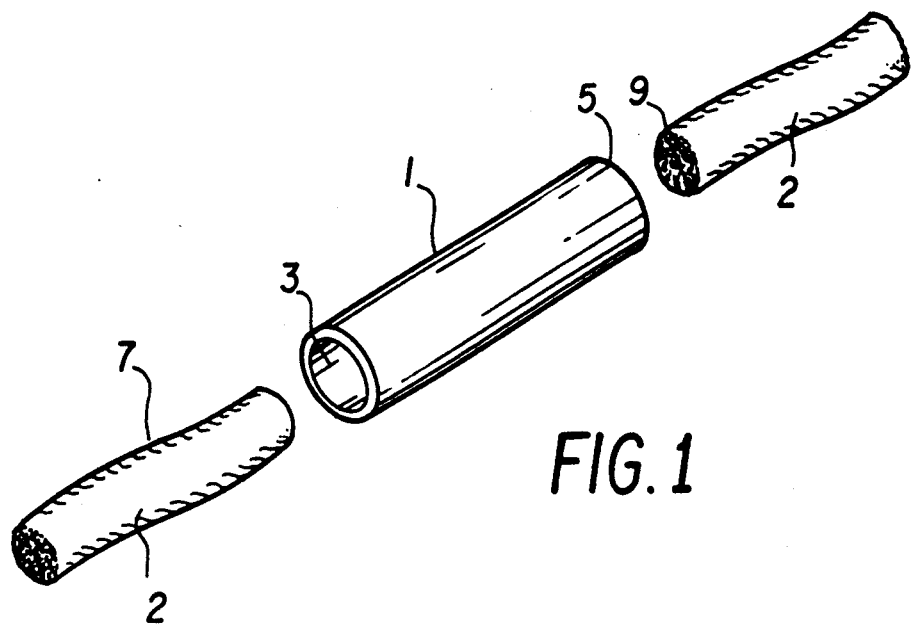
FIG. 1 illustrates the nerve channel embodiment of the present invention for resecting severed ends of a nerve.

The device of the present invention may be fabricated into various forms depending on intended use. Some contemplated forms include solid products such as orthopedic pins, clamps, screws, or plates, clips, staples, vascular implants or supports and nerve channels or supports. Other medical devices could include fibrillar products, knitted, woven or felted such as velours, burn dressings, hernia patches, absorbant papers or swabs, medicated dressings, facial substitutes, gauze, fabric, sheet, felt or sponge for hemostasis, dental packs and breast prostheses. A good description of the formation of bioresorbable materials as matted surgical dressings may be found in U.S. Pat. No. 3,937,223 to Roth. The present improvement could also be useful for bioresorbable polymers in the form of a flake or powder for burns or abrasions, foam, film spray for prosthetic devices, and slowly digestible ion-exchange resins and slow release devices in the form of pills or pellets.

Particularly useful are tubes of varying shapes, lengths and diameters, to be implanted temporarily or permanently. Of these tubular protheses may be mentioned vascular and nerve guidance channels and the like. In the case of the nerve guidance channel, the particular configuration of such tubes may vary according to the size and shape of the nerve to be repaired, and whether the intended repair is to take place in human surgery or in surgery involving other animal species.

With respect to nerve guidance channels, U.S. Pat. No. 3,833,002 to Palma discloses various sizes and shapes that may be employed. Lengths of the tubes, internal diameters, and tubular wall thicknesses may vary according to intended use. The length of the tube would ordinarily be commensurate with the size of the gap to be repaired, also allowing extra tubing in which to insert nerve stumps. The present inventors have found that particularly useful internal diameters commonly range from 0.013 mm to 5.00 mm. It is also desirable to obtain tubes whose wall thicknesses fall within a specific range, such as 0.08 mm to 3.0 mm. A preferred range is 0.5 mm to 1.5 mm in thickness.

The bioresorbable polymers of the invention include homopolymers, copolymers and mixtures thereof, made from "Kreb's cycle acids" or materials capable of metabolism in biological systems through the Kreb's cycle. Such materials include homopolymers or copolymers derived from carboxylic acids, such as those derived from alpha hydroxy carboxylic acids and dicarboxylic acids. Illustrative of these polymers are homopolymers derived from succinic acid, fumaric acid, oxaloacetic acid, L-malic acid, D-malic acid, glycolic acid, L-lactic acid, D-lactic acid, and any combination. Exemplary of still other useful materials are terpolymers derived from the condensation of a dicarboxylic acid, an alpha hydroxy carboxylic acid, and an aliphatic diol, as for example, those described in U.S. Pat. No. 4,481,353 to Nyilas et al., herein incorporated by reference insofar as it pertains to the present invention, as mixtures of such terpolymers with other polymers which are derived from a carboxylic acid.

In the preferred embodiments of the invention, the bioresorbable material is a terpolymer either alone or in conjunction with one or more of the other polymers derived from carboxylic acids or alpha hydroxy carboxylic acids, and mixtures of two or more polymers derived from alpha hydroxy carboxylic acids such as lactic acid.

It is particularly preferred in some cases to mix these terpolymers with polymers of alpha hydroxy carboxylic acids, particularly polymers derived from lactic acid. Illustrative of the most preferred polymer mixtures are terpolymers derived from 1,4 butylene diol (1:1), D,L-lactic and an hydroxy succinic acid, terpolymers derived from 1,6 hexylene diol (1:1) L-lactic acid and succinic acid, in combination with polymers derived from L-lactic acid, D,L-lactic acid, and other isomers thereof. Most preferred for use are polymeric mixtures of poly L-lactide and poly D,L-lactide.

As used herein, the term "polylactide" is equivalent to "poly (lactic acid)" as meaning a polymer of lactic acid. In particular, DL-lactide is a lactide derived from a roughly racemic mixture of lactic acid, and this nomenclature is interchangeable with (DL) lactic acid. Similarly, the terms polyglycolide and poly (glycolic acid) are equivalent.

In some preferred embodiments, the desired weight average molecular weight range of the polymer components, whether used alone or as a combination, is greater than about 150,000. A preferred range is about 150,000-500,000. More preferred is a range of about 75,000-350,000. Most preferred is a molecular weight range of about 200,000-250,000.

The polymerization process may be carried out in such a manner as to achieve the polymer molecular weight range discussed above. For example, in the case of polylactide to be used alone or in a mixture with other polymer components, polymerization of the monomeric lactide units can be effected by any acceptable process, such as by using ring opening polymerization, and the like. It is preferred to use a melt polymerization procedure with stannous octoate as the polymerization catalyst, as it is postulated that the polymer molecular weight increases and molecular weight distribution decreases with its use. When using stannous octoate as the catalyst, the requisite parts per million (ppm) range from about 5 to about 800. A preferred amount is about 75 ppm–200 ppm. Reaction time ranges from about 4 hours to about 168 hours, with 6 hours being preferred. Reaction temperatures range from about 75° to 240° C., with about 180° C. being preferred.

To obtain polymers of different molecular weight, fractional precipitation of the polymer can be achieved using a "good-solvent" such as chloroform or dioxane and a "non-solvent" such as water, methanol, or the like. Polymers of narrow molecular weight distribution are also obtainable in this manner.

Polymers are generally polydisperse or heterogeneous in molecular weight. To improve the physical properties of a polymer product, it is thus desirable to control the molecular weight distribution by the use of fractionation. The molecular weight distribution is commonly calculated as a dispersity number, which is the weight average molecular weight divided by the number average molecular weight (number of polymer units of a particular molecular weight). Dispersity of a polymer for use in implantation devices is preferred to be less than about 10.0; more preferred is a dispersity number of less than about 3.0; most preferred is 1.0–1.9.

Further, polymers of different weight average molecular weights and distribution could be judiciously combined to obtain a material of desired weight average molecular weight and distribution.

A biocompatible plasticizer or plasticizers may be added to impart greater flexibility to the finished device. Such plasticizers include, e.g., but are not limited to, acetyl tributyl citrate, acetyl triethyl citrate, tri-n-butyl citrate, triethyl citrate, and triacetin. In particular, bioresorbable triethyl citrate has been found to be useful.

The polymeric materials of the present invention may also be used in conjunction with biodurable materials. Such a construction may serve as a means of extending the in vivo longetivity of a particular implant. It is contemplated that a composite may be formed by the use of a mixture, or a coating film, or layer, or the like of the bioresorbable polymers of the specific molecular weight range and of a suitable molecular weight distribution with one or more biodurable materials such as silicon, silicon rubber, polyethylene, polyethylene terephthalate, polyfluoroethylene, polyphosphazene, polyurethane, segmented polyurethane, or the like. For some applications, such as the nerve channel, it is preferred that the bioresorbable material form a continuous medium of the device.

The desired devices may be formed from the polymer by any suitable means including solution formation or heat formation. When mixtures are employed, any number of polymers may be physically combined, depending on intended use. In some embodiments, poly DL-lactide is mixed with terpolymers such as those discussed above, or poly L-lactide. Amounts of poly D,L lactide used in this case generally ranges from about 50% to about 1%, preferably about 40% to about 5%, more preferably 30% to about 5%. When poly DL-lactide is mixed with poly L-lactide, these same ranges are preferred. In either case, any combination of molecular weights is within the contemplation of the present invention. Hence, each of the components can be of a molecular weight greater than about 150,000 or each less than about 150,000, or any combination thereof, depending on the desired overall molecular weight.

In general, standard polymer processing techniques can be used to fabricate devices for implantation into living tissue. Hygenic and clean-room conditions for manufacturing of medical articles should be followed. For example, when solution formation is utilized, polymer solutions are commonly filtered before use in a laminar-flow hood to insure that the devices are prepared under clean-room conditions.

The devices of the present invention are particularly suited to be used in conjunction with growth or "tropic factors", which are preferred to encourage the growth and survival of various classes of cells in tissue culture, these factors most often being macromolecular proteins. Implants maintain the structural integrity in the face of the degradative effects of the growth factors which cause premature hydrolysis, cellular infiltration, and swelling. This is particularly notable in tubular conduits where the lumen of the tubes may collapse more readily with the addition of these factors. Of particular interest are neuronotrophic factors for use in layered implantable nerve conduits. Of these growth factors may be mentioned such substances as collagen, fibrinogen, fibronectin, and laminin.

These substances may be obtained in pure form, or mixed with each other or mixed with some neutral carrier such as gelatinous material and the like. Combinations of growth factors are also within the contemplation of the invention.

Using a tubular device as an example, tropic factors may be added to the innermost internal lumen of the tube itself in amounts sufficient to enhance the regeneration of tissue upon implantation. The tropic factor is added prior to implantation of the device, usually in sufficient amount to coat the inside of the tube itself, by any convenient technique, such as for example, injection filling that coats the inner surface or completely fills the lumen. Concentrations of approximately 0.01 mg/ml to 100 mg/ml, and particularly 0.1 mg/ml to 10 mg/ml have been found to be particularly useful.

The devices of the present invention may also be sterilized by means of the techniques usually employed by surgery as long as extensive decomposition of the material does not result. For example, sterilization with ethylene oxide at room temperature may be employed.

The following examples illustrate certain preferred embodiments of the invention and are not definitive of scope.

POLYMER PREPARATION EXAMPLE I

A catalyst solution containing 2.49mg/ml of stannous octoate dissolved in THF was prepared. Two mls of the stanneous octoate solution was added to 25 g of DL-lactide to achieve 200 parts per million. This mixture was then heated under an inert atmosphere for 6 hours at 180° C. The molecular weight average of the resulting polymer was determined to be approximately 178,000 in the absence of solvent weight. Molecular weight was determined by gel permeation chromatography, calibrated against polystyrene standards in THF.

POLYMER PREPARATION EXAMPLE II

Preparation of high molecular weight poly(DLlactide) was effected as follows.

Seventy four grams of recrystallized DL lactide was charged to a Teflon ® reactor along with 74 )1 of 10% stannous octoate in toluene. The reactor was fitted with a nitrogen inlet, thermocouple and an anchor stirrer. The vessel contents were heated by means of an oil bath. A Servodyne gauge and chart recorder were used to monitor the viscosity of the polymer melt.

After stirring for 70 minutes under a nitrogen blanket, the viscosity rose rapidly. The oil bath temperature was held at 190°-200° C. for five hours while the internal thermocouple registered 155° C.

A 30 g aliquot of the polymer was dissolved in acetone and then precipitated with water in a Waring blender. The recovered solids were washed thoroughly with methanol and further granulated in a Waring blender. Finally, the solids were dried in a vacuum oven for 2 days at room temperature, and 24 g of polymer were recovered. Reduced viscosity of the polymer was hsp/c 2.10, 0.1% in dioxane.

The molecular weight average was determined by gel permeation chromatography to be approximately 207,000 in the absence of solvent weight.

Polymers of various molecular weights and distribution were obtained by fractional precipitation.

IMPLANTATION DEVICE PREPARATION EXAMPLE I

Nerve channels composed of polymers prepared substantially as above, ranging in molecular weight from about 177,000 to about 320,000, were readily prepared by the usual multiple solution dipping method using inert metal mandrels or glass mandrels for dipping. Polymer with a weight average molecular weight normally of about 90,000 was obtained commerically (Polyscience). Nerve channels were then prepared from a fractionation, with a weight average molecular weight of 113,000, to serve as a comparison. A THF solution of the polymer was normally used with a plasticizer. Polymer solutions were filtered in a laminar-flow hood before use.

Alternatively, the standard method of melt extrusion of polymers was applied to these polymers to obtain tubings of the desired size.

In either case, clean-room conditions were maintained during the preparation of the nerve channels.

FIG. 1 illustrates a perspective view of a nerve guidance channel prepared according to the present invention, into which severed nerve ends may be inserted. Shown therein is a cylindrical nerve guidance tube 1 having open opposite ends 3 and 5 into which severed distal nerve end 7 and severed proximal nerve end 9 may be inserted. After the nerve ends are inserted into the tube, they may be surgically sutured in place with sutures commonly available.

IMPLANTATION STUDIES

A. Mouse Sciatic Nerve Regeneration

Figure 2:
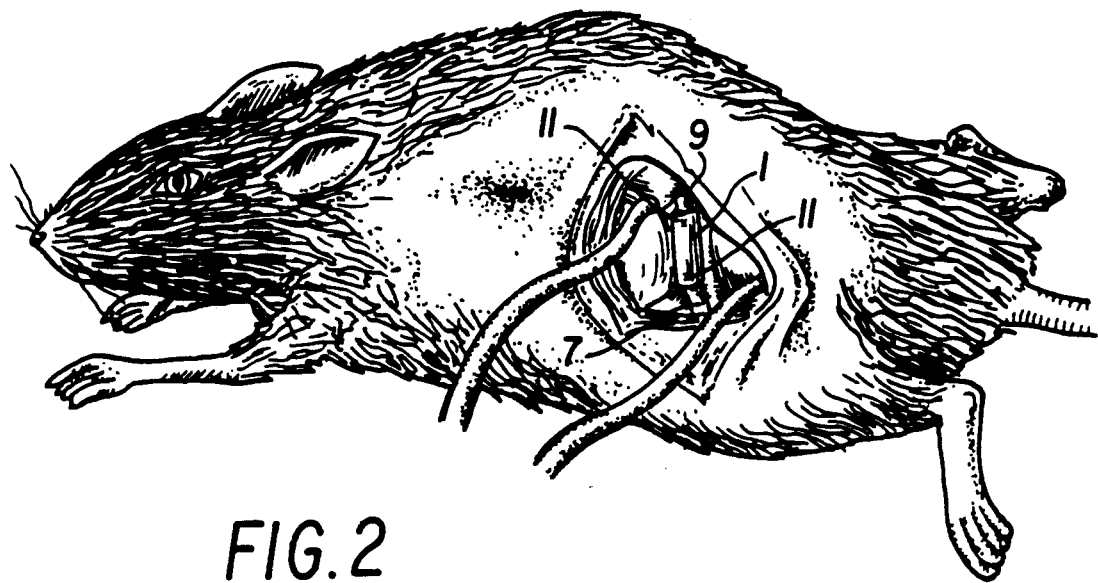
FIG. 2 is a laboratory animal with a nerve channel bridging a severed sciatic nerve, used in nerve regeneration studies.

FIG. 2 further illustrates the experimental design of the mouse sciatic nerve regeneration study. Therein is shown an adult anesthetized C57BL/6J mouse with a sciatic nerve 2 transected and with nerve guide 1 in place. In each mouse, both the proximal stump 9 and distal stump 7 (detailed in FIG. 1) were secured by a single 10–0 nylon suture 11 and were inserted into a 5–6 mm length of nerve guide tube 1 to give a final gap length of 3–4 mm. The tubes were composed of poly (DL-lactide) of molecular weights of about 177,000, 234,000, or 320,000. Poly (DL-lactide) tubes with a molecular weight of approximately 113,000 were inserted into other mice for comparison purposes. At 2, 4 or 6 weeks postoperatively, the sciatic nerve of the animal, appropriately perfused for tissue studies, was again exposed and retransected 3 mm distal to the nerve guide tube. Nerve guides with enclosed regenerated nerves were then dissected out, post-fixed in 2% osmium tetroxide and processed for plastic embedding (DER, Ted Pella Inc.). Just before embedding, the tissue was divided into several segments for sampling at multiple cross-section levels. For most implants, five levels were sampled by one micron sections. These levels were: proximal sciatic stump at 1 to 2 mm proximal to the implant; three levels- (proximal, central, distal) within the tube 1 through the original gap, and the distal stump 1 to 2 mm distal to the implant. Data obtained in the central section was used for comparison. The number of myelinated axons in these sections was determined with a computer-control system. Selected blocks were then resectioned for electron microscopy.

The following table summarizes the myelinated axon count of regenerated sciatic nerve (through the 3–4 mm gap) of the study:

| Polymer (MW) | 2-Week | 4-Week | 6-Week |
|---|---|---|---|
| 113K | 0 | 304 ± 102 (N = 5) | 627 ± 185 (N = 5) |
| 177K | 0 | 827 ± 188 (N = 5) | 759 ± 512 (N = 4) |
| 234K | 0 | 1457 ± 124 (N = 3) | 1844 ± 429 (N = 5) |
| 320K | 0 | 821 ± 416 (N = 3) | 1637 ± 418 (N = 5) |

K = MW × 1000
N = No. of animals

POLYMER PREPARATION EXAMPLE III

HT POLY [1,6-HEXYLENE-(1:1)-L-LACTATE/SUCCINATE-(CODE #134-46)]VIA INITIAL DIRECT ATMOSPHERIC CONDENSATION

The hexylene moiety is used to increase olefinic or aliphatic character of the desired copolymer.

38.0 g (0.20 M) of Succinyl L-lactate was put in a polymerization tube with 18.0 g (0.20M) of 1.6 Hexylenediol (Aldrich Chemical Catalog No. H 1,180-7).

Heat was applied to 112° C. and gradually raised to 187° C.±10° C. in an oil bath for 24 hours.

The polymer was reprecipitated with $H_2O$ from tetrahydrofuran. The molecular weight distribution by GPC with tetrahydrofuran is:

No. Avg. $4.500 \times 10^3$
Wt. Avg. $9.744 \times 10^3$
Disp. = 2.165

IMPLANTATION DEVICE PREPARATION EXAMPLE II

Nerve channels composed of polymers prepared substantially as above were readily prepared by a multiple solution dipping method using inert metal mandrels or glass mandrels for dipping. Polymer with a weight average molecular weight normally of about 90,000 was obtained commerically (Polyscience). Nerve channels were then prepared from a fractionation, with a weight average molecular weight of 113,000, to serve as a comparison. A THF solution of the polymer was normally used with another plasticizer. Polymer solutions were filtered in a laminar-flow hood before use.

Alternatively, the standard method of melt extrusion of polymers was applied to these polymers to obtain tubings of the desired size.

In either case, clean-room conditions were maintained during the preparation of the nerve channels.

Nerve channels were prepared in the manner described above with the following compositions and implanted into mice with severed sciatic nerves as described in IMPLANTATION STUDIES.

POLYMER PREPARATION EXAMPLE II

1) Material 90% L-PDLA, 10% 134-46
O.D 1.19-1.21 mm
I.D. 0.75 mm
L 10 mm
2) Material 90% L-PDLA, 10% 134-46
O.D. 0.88-0.91 mm
I.D. 0.50 mm
L 10 mm
1) 95% L-PDLA 5% 134-46
I.D. 0.75 mm
X O.D. 1.18
L 10 mm
2) 95% L-PDLA 5% 134-46
I.D. 0.50 mm
X O.D. 0.83
L 10 mm
3) 95% DL-PLA 5% 134-46-
I.D. 0 0.75 mm 080 mm
X O.D. 1.12
L 10 mm
4) 95% OL-PLA 5% 134-46
I.D. 0.50
X O.D. 0.86
L 10 mm

Q 4

The following table summarizes the myelinated axon counting results:

| Polymer Composition (MW) | 4-Week | 6-Week | 12-Week |
|---|---|---|---|
| 75% PDLA (100K) 25% BLAHS | 1646,821 | | |
| 75% PDLA (234K) 25% PLLA (229K) | 708 ± 88 N = 3 | 1386 ± 667 N = 5 | 1955 ± 922 N = 5 |
| 90% PDLA (234K) 10% PLLA (229K) | 982 ± 438 N = 5 | 1624 ± 555 N = 5 | 2025 ± 652 N = 4 |
| 95% PDLA (100K) 5% HLASs | 2379 (76) N = 3 | | |

K = MW × 1000
N = No. of animals
BLAHS = Copoly [1,4 butylene (1:1) D,L lactide/D,L hydroxy succinate]
HLAS = Copoly [1,6 hexylene (1:1) L-lactide/succinate]

Similarly, nerve channels of a mixture of poly d,l-lactide with l-lactide and d,l-lactide were prepared and implanted into rats. Before implantation, the lumen of the channels were treated by addition of the growth factor collagen. The myelinated axon count result determined at mid tube, at 8-weeks post implantation, is presented in the following table:

| | Polymer | Myelinated Axon Count (8 week) |
|---|---|---|
| (1) | Poly d,l-lactide (234 KMW) | 8820 ± 1091 (N = 3) |
| (2) | 75% Poly d,l-lactide (177 KMW) 25% Poly l-lactide (229 KMW) | 9393 ± 1526 (N = 4) |

What is claimed is:

1. In an improved device suitable for implantation into a living organism said device capable of encouraging cellular growth and regeneration of function, the improvement which comprises all or a portion of said device comprised of a mixture of one or more bioresorbable polymers selected from the group consisting of a mixture of two or more bioresorbable homopolymers derived from the polymerization of alpha-hydroxy carboxylic acids, and a mixture of one or more bioresorbable terpolymers derived from the condensation of a dicarboxylic acid, an alpha hydroxy carboxylic acid and an aliphatic diol and one or more homopolymers derived from the polymerization of alpha-hydroxy carboxylic acids, said homopolymers and said terpolymers having an average molecular weight equal to or greater than about 150,000 as measured by gel permeation chromatography and wherein at least one of said homopolymers and said terpolymers has an average molecular weight of from about 234,000 to about 320,000 as measured by gel permeation chromatography.

2. The device of claim 1 wherein at least one of said polymers is poly(lactide).

3. The device of claim 2 wherein said poly(lactide) is poly(DL-lactide).

4. The device of claim 3 wherein said mixture comprises two polymers one of which is poly(DL-lactide and the other of which is poly(l-lactide).

5. The device of claim 1 which is a nerve channel which comprises a tubular body.

6. The nerve channel of claim 5 wherein the mixture of bioresorbable polymers is in a form of a thin coating over a biodurable material.

* * * * *